United States Patent [19]

Sato et al.

[11] 4,001,757
[45] Jan. 4, 1977

[54] METHOD FOR DETECTING A REDUCING MATERIAL IN A GAS PHASE

[75] Inventors: Tomi Sato, Neyagawa; Yoshio Iida, Suita, both of Japan

[73] Assignee: Matsushita Electric Industrial Co., Ltd., Osaka, Japan

[22] Filed: Aug. 12, 1974

[21] Appl. No.: 496,860

[30] Foreign Application Priority Data

Aug. 14, 1973  Japan ............................ 48-91493

[52] U.S. Cl. ........................ 338/34; 23/254 E; 29/620; 73/23
[51] Int. Cl.² .............................................. G01N 27/12
[58] Field of Search ............ 73/27 R, 23; 338/34, 338/35; 324/65 R, 715 N; 340/237 R, 237 S; 23/232 E, 254 E; 29/620, 621

[56] References Cited

UNITED STATES PATENTS

| 3,271,719 | 9/1966 | Ovshinsky | 338/34 |
|---|---|---|---|
| 3,343,075 | 9/1967 | Ovshinsky | 338/34 |
| 3,507,145 | 4/1970 | Loh | 73/27 R |
| 3,716,337 | 2/1973 | Jones | 23/232 E |
| 3,725,836 | 4/1973 | Wada et al. | 29/620 |
| 3,754,987 | 8/1973 | Purdes | 29/620 |
| 3,778,229 | 12/1973 | Webster et al. | 73/27 R |
| 3,793,605 | 2/1974 | Fehlner | 338/34 |

OTHER PUBLICATIONS

Seiyama et al., *Analytical Chemistry*, "Study on a Detector for Gaseous Components Using Semiconductive Thin Films," vol. 38, No. 8, pp. 1069–1073, July 1966.

*Primary Examiner*—Richard C. Queisser
*Assistant Examiner*—Stephen A. Kreitman
*Attorney, Agent, or Firm*—Wenderoth, Lind & Ponack

[57] ABSTRACT

A method for detecting the presence of a reducing material in a gas phase which involves heating a gas sensor, which has, as a major part, a partially dehydrated iron hydroxide having electrodes applied thereto, to a temperature less than 500° C and bringing the gas sensor in contact with the gas phase of the reducing material or a gaseous mixture containing the reducing material. The gas sensor can be easily fabricated, and when exposed to a reducing material it undergoes a rapid decrease in electric resistance.

6 Claims, 1 Drawing Figure

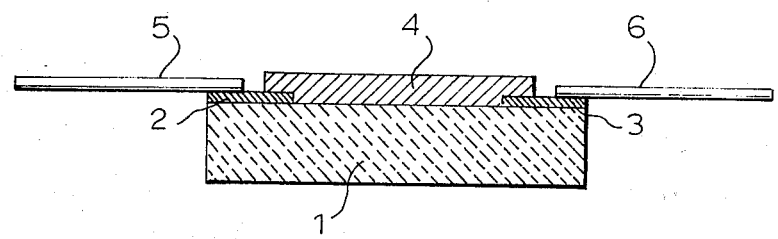

METHOD FOR DETECTING A REDUCING MATERIAL IN A GAS PHASE

This invention relates to a method for detecting the presence of a reducing material in a gas phase and more particularly to a method for detecting the presence of a reducing material in a gas phase comprising heating a gas sensor comprising a solidified product derived from iron hydroxide.

Electroconductive materials such as semiconductors, metals and metal oxides have been known to be sensitive to reducing gases. They undergo a change in electrical resistance upon being placed in contact with the gases. The methods of making gas sensors from these materials and the resulting sensors are practically the same as those of the usual resistors and photosensitive resistors which are widely used in electronic circuits. Composite materials obtained by dispersing electroconductive particles such as carbon black or metal powders in organic polymer compounds can also be used as gas sensitive materials.

There are many needs for a gas sensor characterized by a high and rapid change in the electrical resistance and which is easy to fabricate.

An object of this invention is to provide an easy method for of detecting reducing gases.

This object will be apparent from a consideration of the following detailed description taken together with the accompanying drawing which is a cross-sectional view of a gas sensor according to the present invention.

Before proceeding with a detailed description of the method for detecting the presence of a reducing material in a gas phase contemplated by the present invention, the construction of a gas sensor will be described with reference to the drawing. In this drawing, an insulative substrate 1 such as alumina ceramic is provided, at two different spaced sites on a surface thereof, with electrodes 2 and 3. The electrodes 2 and 3 may be applied to the surface by any suitable and available method, for example, by firing-on commercially available silver electrode paint. A solidified product 4 which is partially dehydrated iron hydroxide is prepared on the surface of the substrate and in contact with the electrodes 2 and 3. Wire leads 5 and 6 are attached conductively to the electrodes 2 and 3, respectively, by a suitable method, for example, by welding.

The method for detecting the presence of a reducing material in a gas phase according to the present invention comprises heating a gas sensor comprising, as a major part, a solidified product which is partially dehydrated iron hydroxide and having electrodes applied thereto to a temperature less than 500° C and bringing said gas sensor in contact with said gas phase of the reducing material whereby said gas sensor undergoes a rapid decrease in the electrical resistance.

The reducing materials referred to herein are fuel gases such as propane, city gas, butane, vapour of alcohols, ethers and esters, liquid petroleum gas, and a mixture of, at least one of the foregoing with air, nitrogen or argon.

According to the present invention, said gas sensor is heated preferably to a temperature of 200° to 300° C for a higher sensitivity to the reducing material in the gas phase. The higher sensitivity referred to herein is the higher and more rapid decrease in the electrical resistance when the gas sensor is brought in contact with said reducing material in the gas phase.

According to the present invention, a better result can be obtained when said solidified product which is partially dehydrated iron hydroxide is made of a precipitate from an aqueous solution containing, as a major solute, a water soluble ferrous compound.

Further according to the present invention, said solidified product consists of, as a minor part, an element selected from the group consisting of copper and bismuth.

Said solidified product can be used for a gas detecting sensor in the form of a thin film and in bulk.

In general, iron hydroxides can be expressed by chemical formulas $Fe(OH)_3$ and $Fe(OH)_2$, and their preparation methods have been well known in the prior art. For example, colloidal ferric hydroxide can be precipitated by adding an alkaline solution to an aqueous solution which contains ferric ions. Ferrous hydroxide can be obtained by treating ferrous ions in the same way as the ions of ferric hydroxide. However, in this case an inert atmosphere should be employed throughout the procedure to prevent the oxidation of ferrous ion into ferric ions in a per se well known way.

Said solidified product can be obtained by gradually heating the iron hydroxides at a relatively low temperature. This heating process causes a partial dehydration of the hydroxides and the formation of a polymer-like product which is very advantageous for the fabrication of the gas sensor. By using this product, a gas sensor contemplated by the present invention can be prepared as follows:

A slurry paste is prepared by mixing said iron hydroxides with a suitable liquid such as water, alcohol or ester. For the preparation of a film type gas sensor, said slurry paste is applied to a suitable insulative substrate such as alumina ceramic. For a bulk type gas sensor, said slurry paste is injected into a case just like casting in a mold. It is, of course, necessary to control the viscosity of the slurry paste in accordance with the type of the gas sensor. In order to evaporate the liquid from the paste and to solidify the hydroxides, it is necessary to heat the applied or cast slurry paste at a temperature of 150° to 500° C. A pair of electrodes is applied to the surface and wire leads are attached conductively to the electrodes by a connection means such as solder or the like.

The slurry paste can be solidified at a low temperature, for instance, at 150° C. It is preferable, however, to solidify it at about 250° C because a low solidifying temperature such as 150° C results in a low sensitivity to gas. The sensor can be used at a working temperature less than 500° C and higher than room temperature. Hence, it is more preferable to solidify at a temperature higher than the working temperature to secure a longer working life.

A gas sensor according to the present invention has a markedly high sensitivity to gases when it is prepared from iron hydroxide which is precipitated from an aqueous solution containing, as a major solute, a water soluble ferrous compound.

In order to achieve a better result in the sensor characteristics such as electrical properties, sensitivity to gases, mechanical strength and surface state, it is desirable to add a minor component such as copper hydroxides or bismuth hydroxide to the iron hydroxides. The solidifying temperature for these compositions depends on the amount of the minor component. The upper limit of the temperature for solidifying is 500° C in case of pure iron hydroxides, 360° C in case of iron hydroxide containing copper hydroxide, and 400° C for iron hydroxide containing bismuth hydroxide, respectively.

EXAMPLE

Iron hydroxide is precipitated by adding aqueous ammonia water to an aqueous solution of ferrous sulfate. The precipitate is washed with water by careful decantation and separated from the solution by means of a centrifuge. A slurry paste is prepared by mixing 100 parts of the hydroxide with 40 parts of n-octyl alcohol. The slurry paste is applied to one surface of a forsterite plate which has previously been provided, at two different spaced sites of the surface thereof, with a pair of parallel electrodes by firing-on platinum electrode paint. The size of the forsterite is 10 × 10 × 2 mm and the distance between the electrodes is 4 mm. The applied slurry paste is heated in air slowly to 320° C and is kept at the temperature for 30 minutes. The thickness of the solidified layer is about 8 $\mu$m. A gas sensor is obtained by attaching wire leads to the electrodes by welding. The gas sensor is kept in a dry commercial nitrogen gas flow of 200 ml/min. at 270° C. Under these circumstances the resistance of the sensor is 800 k$\Omega$. By introducing a nitrogen gas containing 0.1 % of propane fuel gas, the gas sensor undergoes a rapid decrease in the electrical resistance of 80 %.

What is claimed is:

1. A gas sensor for detecting the presence of a reducing material in a gas phase, comprising a base of electrically insulating material, a pair of spaced electrodes on said base, and a body of solidified product comprised of partially dehydrated ferrous hydroxide on said base and bridging said electrodes and in electrical contact therewith.

2. A gas sensor as claimed in claim 1 in which the partially dehydrated ferrous hydroxide is ferrous hydroxide which has been heated to a temperature less than 500° C so as to obtain a solidified product comprised of partially dehydrated ferrous hydroxide.

3. A gas sensor for detecting the presence of a reducing material in a gas phase, comprising a body of a solidified product comprised of partially dehydrated ferrous hydroxide and a pair of electrodes electrically connected to said body at spaced points thereon.

4. A gas sensor as claimed in claim 3 in which said solidified product consists of partially dehydrated ferrous hydroxide.

5. A gas sensor as claimed in claim 3 in which said solidified product is a mixture of partially dehydrated ferrous hydroxide as a major part, and a further material taken from the group consisting of partially dehydrated copper hydroxide and partially dehydrated bismuth hydroxide.

6. A gas sensor as claimed in claim 3 in which the partially dehydrated ferrous hydroxide is ferrous hydroxide which has been heated to a temperature less than 500° C so as to obtain a solidified product comprised of partially dehydrated ferrous hydroxide.

* * * * *